(12) United States Patent
Li et al.

(10) Patent No.: US 8,558,004 B2
(45) Date of Patent: Oct. 15, 2013

(54) REAGENTS AND KITS FOR DETECTION OF INFLUENZA VIRUS AND THE LIKE

(75) Inventors: Xing-Xiang Li, Vienna, VA (US); Tianxin Wang, Boyds, MD (US)

(73) Assignee: Cellex, Inc., Rockville, MD (US)

( * ) Notice: Subject to any disclaimer, the term of this patent is extended or adjusted under 35 U.S.C. 154(b) by 0 days.

(21) Appl. No.: 13/019,737

(22) Filed: Feb. 2, 2011

(65) Prior Publication Data

US 2011/0189655 A1 Aug. 4, 2011

Related U.S. Application Data

(63) Continuation of application No. 12/121,213, filed on May 15, 2008, now Pat. No. 7,893,272.

(60) Provisional application No. 60/930,207, filed on May 15, 2007, provisional application No. 60/999,166, filed on Oct. 16, 2007.

(51) Int. Cl.
*C07D 277/66* (2006.01)
*A61K 31/428* (2006.01)

(52) U.S. Cl.
USPC ............... 548/178; 514/367; 435/5; 435/8

(58) Field of Classification Search
USPC .................. 548/178; 435/5, 8; 514/367
See application file for complete search history.

(56) References Cited

U.S. PATENT DOCUMENTS

| 5,098,828 | A | 3/1992 | Geiger et al. |
| 5,552,298 | A * | 9/1996 | Akhavan-Tafti ............ 435/28 |
| 7,692,022 | B2 | 4/2010 | Cali et al. |
| 2002/0151087 | A1 * | 10/2002 | Hage et al. .................. 436/517 |
| 2008/0299593 | A1 | 12/2008 | Cali et al. |

* cited by examiner

*Primary Examiner* — Nyeemah A Grazier
(74) *Attorney, Agent, or Firm* — Millen, White, Zelano & Branigan, P.C.

(57) ABSTRACT

The present invention relates to reagents and methods for influenza virus detection. These reagents and methods disclosed in the present invention enable simple, rapid, specific and sensitive detection of influenza virus types A and B. These reagents are N-acetylneuraminic acid-firefly luciferin conjugates which can be cleaved by influenza virus neuraminidase.

10 Claims, 7 Drawing Sheets

REAGENTS AND KITS FOR DETECTION OF INFLUENZA VIRUS AND THE LIKE

CROSS-REFERENCE TO RELATED APPLICATION

This application is a continuation of U.S. patent application Ser. No. 12/121,213, filed May 15, 2008 now U.S. Pat. No. 7,893,272 and claims the benefit of U.S. Provisional Application Nos. 60/930,207, filed May 15, 2007, and 60/999,166, filed on Oct. 16, 2007, which are incorporated herein by reference in their entirety.

TECHNICAL FIELD

The present invention relates to influenza virus detection reagents and kits which use a group of chemicals that can be used for detection of the neuraminidase activity as a method for the detection of influenza viruses present in a sample. The chemicals are conjugates between N-acetylneuraminic acid (sialic acid) or its derivatives and firefly luciferin, which are linked together through a glycoside bond via an —OH group on the sugar ring of the N-acetylneuraminic acid, preferably the 2' position.

The present invention further relates to reagents and test kits for the detection of other enzymes, pathogens or diseases using firefly luciferin containing conjugates as substrates.

BACKGROUND OF THE INVENTION

Influenza is a constant and serious threat to public health. Each year, influenza epidemic leads to 200,000 hospitalizations and 36,000 deaths in the United States. Globally, influenza disease impacts every year up to 10% of the world's population—approximately 500 millions of the people.

An influenza pandemic could lead to far greater number of deaths and economic impact. The 1918 influenza pandemic, for example, killed 20-40 million people in the world and more than 500,000 people in the United States. As medical science advances, there are several drugs that are available for treatment or prophylaxis of influenza A and B. However, the prerequisite for effective treatment or prevention control is rapid, sensitive and specific detection of the viruses at an early stage of individual infection or of an outbreak.

Conventional method for influenza virus detection involves first viral culture of a nasal wash, throat swab specimen, tracheal aspirate secretions, bronchial lavages, or lung tissue. The virus in cultures usually is detected between day 2 and day 5 by performing hemabsorption test, which is normally followed by detection with an immunofluorescence assay (IFA) using type specific antibodies. This test, while reliable, is not suitable for point-of-care use, which requires a test that can produce a test result in a short period of time, e.g., less than 30 minutes.

Consequently, faster influenza virus tests were developed to meet the need of point-of-care use. These tests are of two types. One uses specific antibody or antibodies to detect influenza proteins, or antigens. The other detects the activity of neuraminidase that is present in all type A and B influenza virus. While these tests can generally be completed in a short period of time, e.g., within 30 minutes, they lack sufficient clinical sensitivity, which is generally around 70% when compared to virus culture methods. Lack of clinical sensitivity for these rapid tests appears to be a result of low analytical sensitivity (or limit of detection), which is generally in the range between $10^4$ and $10^5$ $CEID_{50}$ (Egg Infection Dose) or $TCID_{50}$ (Tissue Culture Infection Dose) units of influenza virus. The lack of sensitivity seriously undermines the clinical usefulness of these tests.

More sensitive methods that involve the use of polymerase chain reaction (PCR) for detecting influenza virus nucleic acids have been described in a number of published articles. While these methods provide a more sensitive alternative, they generally have a number of shortcomings that make them less suitable for point-of-care use. For example, these methods generally demand complicate and lengthy sample preparation, which increases not only the cost, but also the time it takes to complete the test. These methods, particularly the so called real time PCR, also require expensive equipment and well-trained technicians, which cannot be afforded by most point-of-care facilities, e.g., the physician's offices.

In an attempt to prepare a reagent that would provide better sensitivity for influenza virus detection, a substrate for chemiluminescent influenza viral neuraminidase detection was synthesized (Analytical Biochemistry 2000; 280: 291-300). The substrate is a conjugate between N-acetyl-neuraminic acid and spiroadamantyl-1,2-dioxetane (herein referred to as dioxetane) through the 2' position of the sialic acid. Cleavage of the linkage by neuraminidase releases the dioxetane, which oxidizes to generate chemiluminescence under alkaline conditions.

Therefore, this substrate could be used for the detection of neuraminidase activity, including that of influenza virus, as a means of detecting a pathogen such as influenza virus.

One shortcoming of the sialic acid-dioxetane substrate or methylated form of this substrate is that the pH for the neuraminidase reaction and chemiluminescence reaction is significantly different (e.g., pH 6.5 vs. pH 11). This makes it necessary to separate these two reactions, which increases the complexity and cost of the assay.

Similar problems also exist for the detection of other pathogens and diseases. Therefore, there is a need for reagents or kits that enables simple, rapid and sensitive detection of influenza virus in a clinical, animal or environmental sample.

SUMMARY OF THE INVENTION

The present invention relates to reagents and methods for influenza virus detection. These reagents and methods disclosed in the present invention enable simple, rapid, specific and sensitive detection of influenza virus types A and B.

One embodiment of the current invention involves the use of an influenza virus capture reagent, which is a solid support coated with an influenza virus binding ligand. The capture reagent enables selective enrichment of influenza virus from a sample. When used in an influenza detection assay, the capture reagent improves the sensitivity of the assay by enriching the influenza virus in a sample. In addition, selective binding of the affinity ligand to influenza virus provides the specificity of the assay even if the downstream detection process is not specific for influenza virus.

Another embodiment of the present invention relates to a group of chemicals that enable the detection of influenza virus by detecting the neuraminidase activity of influenza virus. These chemicals are conjugates between N-acetyl-neuraminic acid (sialic acid) or its derivatives and firefly luciferin, which are linked together through a glycoside bond via an —OH group on the sugar ring of the N-acetyl-neuraminic acid. The preferred position on the sugar ring is the 2' position since this is the glycoside bond favored by influenza neuraminidase. The conjugates used as the neuraminidase substrates can be represented by the following formula (Formula I):

Formula I wherein R1, R2, R3 are each, independently of one another, hydrogen or alkyl groups comprising 1-5 carbon atoms, or a salt thereof.

In one embodiment the alkyl group is a straight chain or branched alkyl group.

In a preferred embodiment, the alky group is methyl.

Suitable salts are those which are compatible with the assays of this invention, and include alkali metal (e.g., sodium, potassium, etc.), alkaline earth metal (e.g., calcium, magnesium, etc), ammonium, etc salts.

Figure 4:
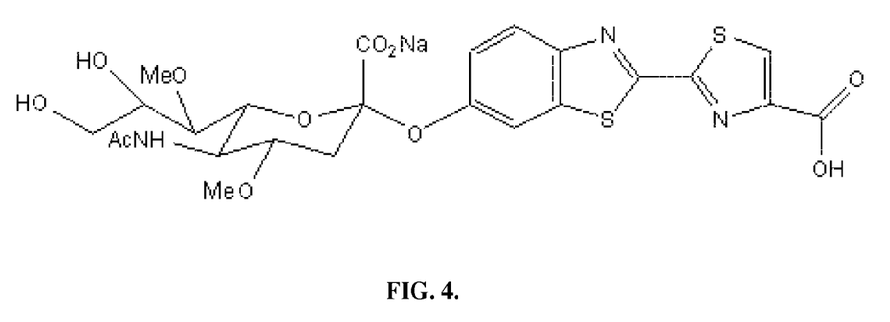
FIG. 4 is a diagram depicting the chemical structure of 4,7 methylated N-acetylneuraminic acid-firefly luciferin conjugate.

In another embodiment at least one of R1, R2, or R3 is not hydrogen. A representative example is shown in FIG. 4.

Components not specifically discussed herein are conventional in the field of the assays of this invention, including chemicals compatible with such assays, e.g., buffers, solvents, etc.

When used for detection of influenza viral neuraminidase activity, the conjugate is incubated under appropriate conditions with a sample to be tested. If the sample contains detectable amounts of influenza virus, the viral neuraminidase cleaves the conjugate and releases firefly luciferin. A second reagent mix, which contains necessary reagents with the exception of firefly luciferin for firefly luciferase catalyzed biochemiluminescence reaction, is added to the neuraminidase reaction. Presence of free firefly luciferin enables the biochemiluminescence reaction, hence the production of light signal, which is indicative of the presence of influenza virus. The light signal can be detected with a luminometer, which is readily available from many commercial vendors (e.g., Promega). With this test design, a test kit contains at least a neuraminidase reaction reagent mix and a biochemiluminescence reaction mix. The detection procedure involves at least two major steps.

Yet another embodiment is combining the viral neuraminidase and luciferase-based biochemiluminescence reactions together in one assay step such that the firefly luciferin cleaved by the viral neuraminidase from the conjugate is immediately consumed by luciferase to give rise to light signal. Because the released firefly luciferin is immediately measured as it is being generated by neuraminidase, this assay format is essentially a real time assay for neuraminidase activity. The real-time assays are generally more quantitative and thus more appropriate for certain applications that require quantitation capability of a neuraminidase assay such as the resistance testing for anti-influenza drugs that target the neuraminidase. Combining the two reactions into one assay step also simplifies the detection procedure, which makes it suitable for point-of-care use. A test kit contains one key reagent component, which is the master mix that contains all necessary reagents for both the neuraminidase and firefly luciferase reactions except for neuraminidase and firefly luciferin. In preferred embodiments, the master mix is lyophilized for long term storage.

The invention provides methods for specific detection of influenza viral neuraminidase for diagnostic. In certain embodiments, inhibitors and antibodies are used to inhibit the neuraminidase activities from undesired sources, e.g., a bacterial species. In other embodiments, the test uses neuraminic acid-firefly luciferin conjugates, e.g., the 4,7 methylated N-acetylneuraminic acid-firefly luciferin conjugate, which favors influenza viral neuraminidase and thereby improves the detection specificity.

The present invention also provides methods for detection of influenza virus using a non-specific substrate. The undesired neuraminidase activity can be inhibited with polyclonal or monoclonal antibodies or with small blocking molecules that are specific for the undesired neuraminidase activity. Alternatively, a sample can be tested in duplicate with two detection reagent mixes, one of which contains influenza viral neuraminidase specific inhibitor, e.g., oseltamivir carboxylate, while the other contains no inhibitor. Presence of detectable influenza virus in a sample is indicated if the detection mix without inhibitor is positive and the inhibitor-containing detection mix is negative. If both are positive, it indicates infection due to certain bacterial species or virus (e.g., parainfluenza virus).

In addition, the present invention provides similar methods for the detection of other enzymes, which may be indicative of a pathogen or disease. For example, sialidase (neuraminidase) is a marker for bacterial vaginosis. Thus, the N-acetylneuraminic acid-firefly luciferin substrate (FIG. 3) can also be used for diagnosis of bacterial vaginosis. Likewise, the pathogen *Trypanosoma cruzi*, which causes Chaga's disease, possesses trans-sialidase (sialic acid transferase), which can also use the N-acetylneuraminic acid-firefly luciferin substrate. Hence, the N-acetylneuraminic acid-firefly luciferin substrate can also be used for detection of active infection of this pathogen. Other substrates and their applications include a beta-galactosaminidase substrate (e.g., firefly luciferin-N-acetyl-beta-D-galactosaminide) for detection of beta-galactosaminidase, a L-proline aminopeptidase substrate (e.g., L-prolyl-6-amino firefly luciferin) for detection of L-proline aminopeptidase, a leukocyte esterase substrate (e.g., carboxylic acid-firefly luciferin or alcohol-firefly luciferin conjugates) for detection of leukocyte esterase, an alpha-L-Fucosidase substrate (e.g., alpha-L-fucopyranoside-firefly luciferin conjugate) for detection of alpha-L-Fucosidase, a lipid esterase substrate (e.g., Octanoate-firefly luciferin conjugate) for detection of lipid esterase, and a hydroxyproline aminopeptidase substrate (e.g., L-hydroxylprolyl-6-amino firefly luciferin) for detection of L-Hydroxyproline aminopeptidase.

Furthermore, the present invention provides a method for reducing the background resulted from the contaminating firefly luciferin in the conjugate. The substrates disclosed in the present invention all contain firefly luciferin moiety in the substrates, which is cleaved by an enzyme to free the firefly luciferin in the conjugate. The freed luciferin enables the firefly luciferase-catalyzed biochemiluminescence reaction, hence the detection of the enzyme. The substrates are synthesized by coupling a specific moiety to firefly luciferin, which is followed by purification to remove unincorporated firefly luciferin and other contaminants. However, the presence of even minute amounts of contaminating free firefly luciferin, e.g., 1 ng per reaction, can still generate significant background. The inventors discovered that a reagent mix containing all necessary reagents and conditions suitable for both the specific enzyme reaction (except for the enzyme itself, which may be present in a sample for detection) and firefly luciferase reaction (except for luciferin) could be prepared in a single mix (the master mix). The master mix can be simply incubated for an appropriate period of time, e.g., overnight at 2-8° C. before lyophilization or freezing or being used for detection, which allows the removal of contaminating luciferin by the firefly luciferase in the master mix.

Coelenterazine and its corresponding enzyme (e.g., apoaequorin and *Renilla* luciferase) can be used instead of firefly luciferin and firefly luciferase. Coelenterazine is found in radiolarians, ctenophores, cnidarians, squid, copepods, chaetognaths, fish and shrimp. Coelenterazine is the light-emitting molecule in the protein aequorin.

BRIEG DESCRIPTIO OF THE TABLES

Table 1: Detection Results of a Bacterial Vaginosis Test Positive Control Using the Detection Mix

DETAILED DESCRIPTION OF THE INVENTIONS

The present invention relates to reagents and methods for neuraminidase activity and influenza virus detection. These reagents and methods disclosed in the present invention enable simple, rapid, specific and sensitive detection of influenza virus types A and B.

Figure 1:
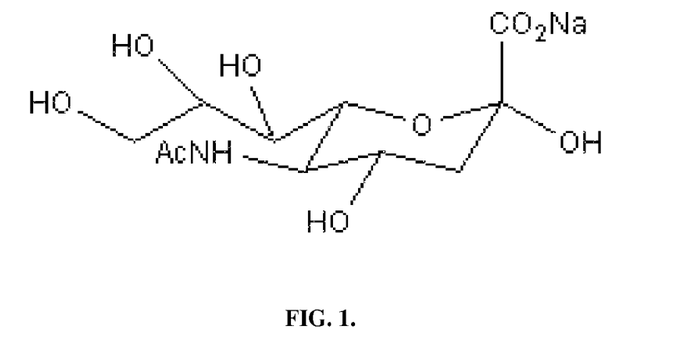
FIG. 1 is a diagram depicting the chemical structure of N-acetylneuraminic acid.
Figure 2:
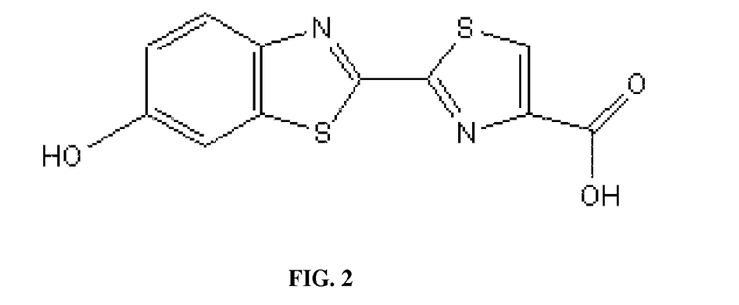
FIG. 2 is a diagram depicting the chemical structure of firefly luciferin.

The present invention utilizes a group of chemicals that enable the detection of influenza virus by detecting the neuraminidase activity of influenza virus. These chemicals are conjugates between N-acetylneuraminic acid (sialic acid) or its derivatives and firefly luciferin. Chemical structures of N-acetylneuraminic acid (sialic acid) and firefly luciferin are depicted in FIGS. 1 and 2.

In the current invention, the term chemiluminescence and bioluminescence are used interchangeably. Firefly luciferin is oxidized in the presence of the corresponding luciferase and other co-factors (e.g., ions and ATP) to produce light.

One important aspect of the current invention is that the N-acetylneuraminic acid-firefly luciferin conjugate (herein frequently referred to as the conjugate) is not necessarily specific for influenza viral neuraminidase. This is because the capture reagent can selectively bind to influenza virus, thereby resulting in specific detection of influenza virus even if the conjugate is not specific for influenza virus. More importantly, this conjugate is a more natural and, potentially more efficient, substrate for neuraminidase as compared to the methylated substrate.

Figure 3:
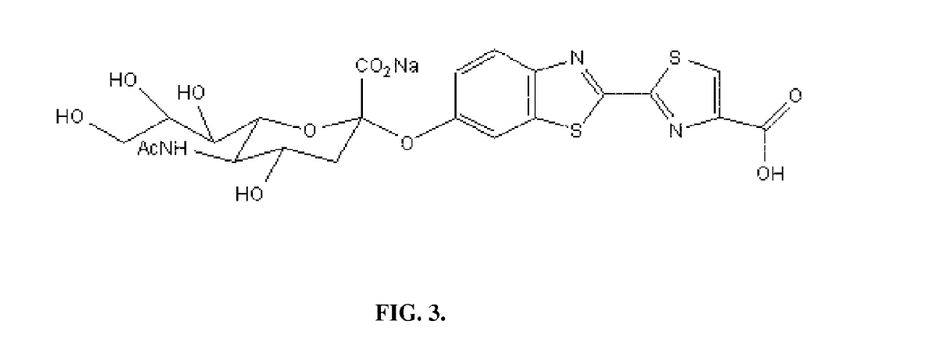
FIG. 3 is a diagram depicting the chemical structure of an N-acetylneuraminic acid-firefly luciferin conjugate.

One preferred embodiment of the N-acetylneuraminic acid-firefly luciferin conjugate is depicted in FIG. 3. The conjugate is linked together via a glycoside bond through the 2' position of N-acetylneuraminic acid and —OH group on the aromatic ring of firefly luciferin. It is understood that variations of such linkage may be appropriate for neuraminidase activity detection. Similarly, derivatives of N-acetylneuraminic acid and firefly luciferin may also be appropriate for neuraminidase activity detection described in this invention. The conjugates used as neuraminidase substrate can be represented by the following formula shown for the Na salt:

wherein R1, R2, R3 are each, independently of one another, hydrogen or alkyl having 1-5 carbon atoms.

A number of organisms express neuraminidase that may hydrolyze the same N-acetylneuraminic acid-firefly luciferin conjugate described above. For example, parainfluenza and certain bacterial species possess neuraminidase. Thus, this class of substrate may not be specific for neuraminidase from a particular organism. Therefore, the reagents and methods described in the current invention can also be used for detection of other sialidases of bacterial, viral, protozoa, and vertebate (including human) origin besides sialidase from influenza virus.

Sialic acid derivatives are also appropriate for use in influenza virus detection provided that the derivatives can form a glycoside with firefly luciferin or its derivatives, and that the conjugate can be cleaved by neuraminidase. Examples of sialic acid derivatives include 4-alkyl or 7-alkyl or 4,7 alkyl N-acetylneuraminic acids (e.g. those described in U.S. Pat. No. 6,303,764 and U.S. Pat. Nos. 6,420,552, 6,680,054). One example (4,7 methylated N-acetylneuraminic acids-firefly luciferin conjugate) is given below in FIG. 4, which has better specificity for flu neuraminidase than for bacterial neuraminidase.

Methods for synthesizing the conjugate depicted in FIG. 3, or similar conjugates, can be derived from existing methods. For example, a method for synthesizing N-acetylneuraminic acid dioxetane conjugate, described in a publication (e.g., Analytical Chemistry 280, 291-300), can be used for synthesis of the conjugate depicted in FIG. 3, or similar conjugates. An example is included in EXAMPLE 1.

Figure 5:
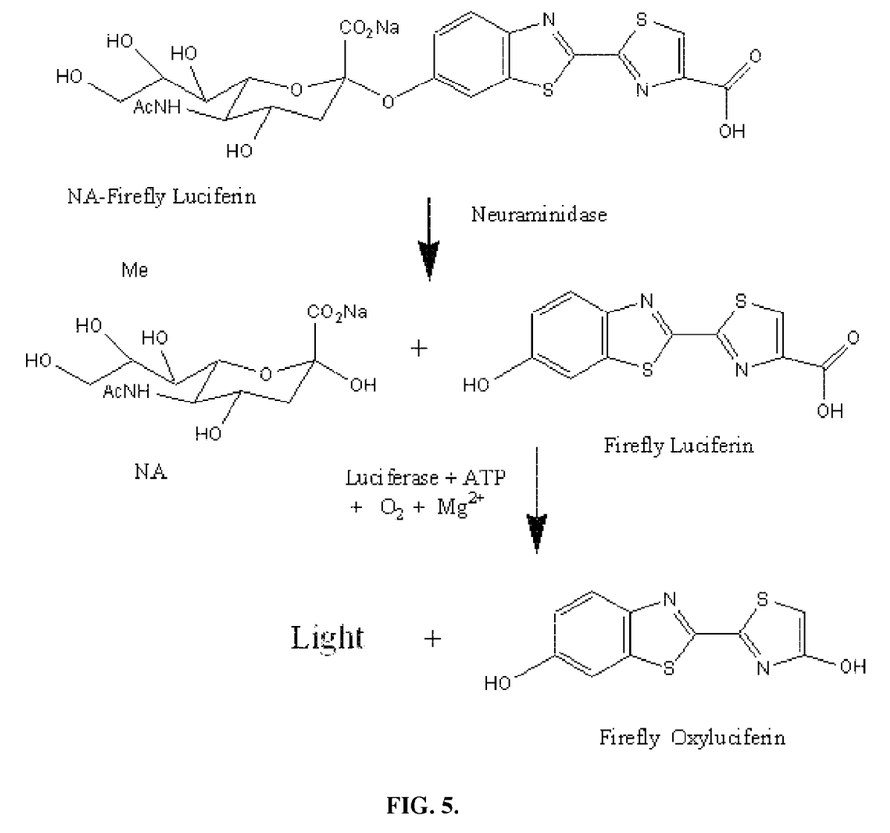
FIG. 5 provides a schematic drawing showing the principle for influenza neuraminidase detection as a means for the detection of influenza virus using the N-acetylneuraminic acid-firefly luciferin conjugate.

The principle for detecting neuraminidase activity using the conjugate is depicted in FIG. 5. The sialic acid-firefly luciferin conjugate is a substrate for neuraminidase, which cleaves the substrate to give rise to free firefly luciferin that is the substrate of luciferase, which is present in the detection mix. The conjugate itself is not a substrate for firefly luciferase. Therefore, the firefly luciferase-catalyzed biochemiluminescence is dependent on neuraminidase activity, which is provided by the influenza virus or its lysate in a sample.

In an influenza virus detection assay using a sialic acid-luciferin conjugate, the sample containing influenza virus is first incubated with the capture reagent. After binding of influenza virus to the reagent, the reagent is washed with wash buffer. The capture reagent, now bound with influenza virus, is suspended with the conjugate mix and then incubated for an optimal period of time and at optimal temperature to allow neuraminidase-dependent cleavage of the conjugate. The capture reagent is then removed using an appropriate means. The supernate is then added to the detection mix, which contains luciferase and other necessary chemicals, and placed in a luminometer to detect the light signal. A more detailed protocol is provided in EXAMPLE 1.

In some embodiments, detection of influenza virus using the conjugate involves essentially three steps: 1) capture of influenza virus using the capture reagent, 2) incubation of the conjugate with the captured virus or its lysate, and 3) detection of the cleaved conjugate by detecting the resulting luciferin using luciferase, which generates the light signal in the presence of luciferin and other appropriate reagents. In certain embodiment, steps 2 and 3 can be combined together as a single step thereby reducing the number of procedure into essentially two. More detailed description of the detection procedures are disclosed in Example 1 and Example 2. An example of the test result is provided in FIG. 6.

In other embodiments, detection of influenza virus using the conjugate involves essentially 2 steps: 1) incubation of the conjugate with the captured virus or its lysate, and 2) detection of the cleaved conjugate by detecting the resulting luciferin using luciferase, which generates the light signal in the presence of luciferin and other appropriate reagents. In certain embodiment, step 1 is eliminated through the use of specific conjugates for influenza viral neuraminidase or inhibitors for nonspecific neuraminidase activities, thereby reducing the number of procedure into essentially one (the step 2).

In one embodiment, the method for detecting influenza virus in a sample comprises essentially three steps: a) virus capture, b) neuraminidase-dependent cleavage of the conjugate to release firefly luciferin moiety, which becomes free firefly luciferin in the presence of neuraminidase in a sample, and c) firefly luciferase-catalyzed biochemiluminescence reaction to detect the released luciferin. The key feature of this method is the separation of neuraminidase reaction from the biochemiluminescence reaction. The corresponding test kit contains three key components (the capture reagent, conjugate mix, and detection mix) and two accessory components (wash buffer and conjugate suspension solution or deionized water). The capture reagent can be a solid support such as magnetic particles, which are coated with influenza virus specific receptors, e.g., monoclonal antibodies against the surface protein hemagglutinin. Examples of compositions for these components are described in EXAMPLE 1. A detection protocol for using this test kit type is described in EXAMPLE 1.

Yet in another embodiment, the method for detecting influenza virus in a sample comprises essentially two steps: a) virus capture, and b) firefly luciferase-catalyzed biochemiluminescence reaction to detect free luciferin as soon as luciferin moiety is cleaved from the conjugate by influenza neuraminidase. The key feature of this method is the combination of neuraminidase reaction with the biochemiluminescence reaction in a single step. This method is therefore referred to as real time detection of influenza neuraminidase or real time detection method since the free luciferin cleaved from the conjugate is immediately consumed by luciferase to give rise to light signal. The test kit used in this detection method contains two key components (the capture reagent and detection mix) and two accessory components (the wash buffer and virus lysis solution). The capture reagent can be the same as that used in the three step procedure.

In the real time neuraminidase detection method, the detection mix contains all necessary chemicals and appropriate buffer for neuraminidase reaction, including the conjugate itself, and for firefly luciferase-catalyzed biochemiluminescence reaction except for firefly luciferin. Examples of the composition for these components are described in EXAMPLE 2. Detection of influenza virus in a sample using this version of the test kit, or variations of it, consists of essentially two steps: 1) capture of influenza a virus in a sample followed by washing and, 2) detection of the captured virus or its lysate using the detection mix. The optimal pH for neuraminidase reaction and firefly luciferase-catalyzed biochemiluminescence, i.e., pH 6.5 vs. pH 7.8, are different. It is surprising that both enzymes have sufficient activity at a mutual pH, e.g., at or around 7, which can be used for the detection mix for both reactions. The combination of the two reactions considerably simplifies the detection procedure. A more detailed detection protocol is described in EXAMPLE 2.

Yet still in another embodiment, the virus capture step is eliminated from the detection procedure, thereby enabling essentially a one-step detection procedure. Specific detection of influenza virus is enabled through the use of one of two approaches or a combination of both. In certain aspects of the current invention, specific detection of neuraminidase from a particular source is achieved using a modified sialic acid moiety of the N-neuraminic acid-firefly luciferin conjugate. Examples of conjugates with modified sialic acid derivatives, e.g., 4-alkyl or 7-alkyl or 4,7 alkyl N-acetylneuraminic acids are specific for influenza viral neuraminidase over bacterial neuraminidase as described in U.S. Pat. Nos. 6,303,764, 6,420,552, and 6,680,054, which are cited here solely for reference. An example of such a conjugate is depicted in FIG. 4.

In another embodiment, the undesired neuraminidase is inhibited using specific antibodies and inhibitors. The undesired neuraminidase activity is inhibited using specific polyclonal or monoclonal antibodies. For example, for detection of influenza viral neuraminidase, the non-specific neuraminidase activity from likely contaminating organisms in the sample such as bacterial species *Streptococcus pneumoniae* and *Actinomyces viscosus* are inhibited using antibodies specific for the neuraminidases from these sources. This approach is possible because neuraminidases from different organisms have distinct amino acid sequences, which permits the generation of species-specific, or sub-species-specific, neuraminidase antibodies. For example, specific antibodies are commonly used to differentiate neuraminidase subtypes of influenza virus in neuraminidase neutralization assays.

The procedure of making these antibodies is well to the skilled in the art. For example, recombinant neuraminidase protein can be produced in *E. coli* by cloning the complete or partial genomic (in the case of bacterial neuraminidase) or cDNA (in the case of eukaryotic neuraminidase) sequences into a bacterial expression vector that preferably contains an affinity ligand, e.g., his-tag, which facilitates the purification of the recombinant protein. Bacterial clones expressing the enzyme can be screened and selected in a chemiluminescence assay using the N-neuraminic acid-firefly luciferin conjugate. If the recombinant enzyme is tagged with an affinity ligand, then appropriate affinity column can be used to purify the enzyme. For example, nickel coated agarose column can be used to purify his-tagged recombinant neuraminidase.

The purified neuraminidase can be used to immunize an animal, e.g., a rabbit, for production of polyclonal antibodies. Alternatively, the protein can be used to immunize mouse from which the B-lymphocytes can be used to generate hybridoma, which can be used for screening a monoclonal antibody that specifically inhibits the neuraminidase.

One or more monoclonal and/or polyclonal antibodies can be used in an assay for inhibiting neuraminidase activities from one or more contaminating sources. For example, polyclonal antibodies or anti-sera or monoclonal antibodies for *Streptococcus pneumoniae, Actinomyces viscosus* and parainfluenza neuraminidases can be used in an assay for detecting influenza viral neuraminidase. It is understood that the amounts of each antibody or anti-serum used in an assay need to be optimized so that the antibodies can maximally inhibit contaminating neuraminidase activities but not the neuraminidase activity to be detected. Likewise, small molecules specific for the undesired neuraminidases, e.g., bacterial neuraminidase, can also be used in fashion similar to the antibodies.

Yet another embodiment involves the use of the neuraminic acid-firefly luciferin depicted in FIG. 3 for specific for influenza virus infection using an influenza viral neuraminidase specific inhibitor such as oseltamivir carboxylate. To perform specific detection of influenza virus in a sample, two forms of the detection mix disclosed in EXAMPLE 2 need to be formulated. One form (Detection Mix 1) contains no influenza neuraminidase inhibitor and the other (Detection Mix 2) contains the inhibitor. For clinical diagnosis, a clinical sample such as nasal swab wash is split into two portions. One portion of the sample is added to Detection Mix 1 whereas the other portion is added to Detection Mix 2, followed by detection of lights signal as described in EXAMPLE 2.

If both are positive, it indicates that the neuraminidase activity in the sample is from a non-influenza virus source, such as bacteria or parainfluenza virus. If Detection Mix 1 is positive and Detection Mix 2 is negative or has significantly reduced signal, then it indicates that there is influenza virus infection. If both are negative, then it indicates that there is no infection with influenza virus or parainfluenza virus. Appropriate influenza viral neuraminidase inhibitors include, but are not limited to, oseltamivir carboxylate, zanamivir, and peramivir.

A preferred embodiment is the real time detection method, which combines the neuraminidase reaction, i.e., cleavage of the conjugate, and firefly luciferase-catalyzed biochemiluminescence reaction together in a single reagent mix. The light signal is measured at real time, i.e., firefly luciferin is detected as soon as it is cleaved from the conjugate by neuraminidase. In this real time detection method, there is no accumulation of free luciferin. Since both the neuraminidase and firefly luciferase catalyzed reactions occur in the same reaction mix, the pH can not be exactly optimal for both neuraminidase and firefly luciferase. This is in contrast with the three step method, where the two reactions are separated, which allows the two reactions to occur at optimal pH (around pH 6.5 for neuraminidase and 7.8 for firefly luciferase) and the released firefly luciferin to accumulate for an extended period of time (e.g., 10 minutes) before being subjected to firefly luciferase-catalyzed biochemiluminescence reaction. Therefore, the signal output with the real time detection method (e.g., 10 seconds) may be lower.

Lower signal output in the real time method can be partially compensated by extending the signal collection time from, for example, 10 seconds to 120 seconds. In addition, lower activity of the firefly luciferase at pH 7.0, which is lower than the optimal pH (pH 7.8), can be partially or completely compensated by adding more luciferase to the reaction mix. Moreover, the background counts is expected to be lower in the real time method since auto-cleavage (i.e., neuraminidase-independent) of the conjugate at lower pH is more severe. Consequently, the signal to background ratio for the real time method is expected to be similar to, or no less than, that for non-real time detection method. Surprisingly, the real time assay as described in EXAMPLE 3 gave excellent sensitivity for the detection of influenza virus.

The real time method offers a number of advantages, including 1) more convenience due to the combination of two reactions in one test tube, 2) better specificity due to real time measurement of the neuraminidase activity, 3) less background because of less auto-cleavage of the conjugate at neutral pH, 4) shorter operation time and therefore faster time-to-result due to the combination of the two reactions into one, 5) more quantitative, and 6) lower cost of manufacturing because there is only one key reagent mix. Thus, the real time detection method is a preferred choice for the detection of influenza virus in many situations such as point-of-care use.

It is understood that influenza virus capture step is not necessary for certain applications. For monitoring influenza virus growth in a culture, for example, the medium can be diluted in an appropriate buffer or water and directly added to the conjugate mix according to the three step protocol described in example 1 or to the detection mix according to the real time protocol described in example 2. Example 3 describes the detection of cultured virus in a solution without virus capture step. When the influenza neuraminidase specific substrate (e.g. the conjugate described in FIG. 4) is used, capture step is not necessary.

It is further understood that the reagents and methods disclosed above are also applicable for the detection of other diseases or pathogens. For example, elevated sialidase activity in vaginal fluid samples is indicative of bacterial infection in vagina, which is known as Bacterial Vaginosis (By). Thus, an embodiment of the current invention is the use of the neuraminic acid-firefly luciferin conjugate depicted in FIG. 3 for diagnosis of BV, which is described in more detail in EXAMPLE 4.

Another embodiment is the use of the neuraminic acid-firefly luciferin conjugate depicted in FIG. 3 for diagnosis of active infection by the parasite *Trypanosoma cruzi*, which causes Chagas' disease. *Trypanosoma cruzi* expresses high levels of trans-sialidase activity, which is a type of sialidase. The neuraminic acid-firefly luciferin conjugate depicted in FIG. 3 can be used to measure trans-sialidase activity and thus used to diagnosis of active infection of this parasite. This application is described in more detail in EXAMPLE 6.

Other applications include a L-proline aminopeptidase assay using L-prolryl-6-amino firefly luciferin as the substrate for detection of the enzyme (EXAMPLE 7), a leukocyte esterase assay using firefly luciferin-alcohol or firefly luciferin-carboxylate esters as substrate for detection of esterase activity (EXAMPLE 8), an alpha-L-fucosidase assay using an alpha-L-fucopyranoside-firefly luciferin conjugate as the substrate for detection of alpha-L-fucosidase (EXAMPLE 9), a glycylproline dipeptidyl aminopeptidase assay using L-glycyl-L-prolyl-firefly luciferin conjugate as the substrate for detection of the enzyme (EXAMPLE 10), a beta-D-galactosaminidase assay using firefly luciferin-N-acetyl-beta-D-galactosaminide as the substrate for detection of beta-galactosaminidase (EXAMPLE 11), a lipid esterase assay using octanoate-firefly luciferin ester for detection of a lipid esterase (EXAMPLE 12), and L-hydroxylprolyl-6-amino luciferin conjugate for detection of L-Hydroxyproline amiopeptidase (EXAMPLE 13).

Within the scope of the present invention is a manufacturing process that results in greatly reduced background light signal. The basic detection principle disclosed in this invention involves the use of firefly luciferase in a chemiluminescence reaction to detect free firefly luciferin, which is cleaved from a firefly luciferin conjugate by a marker enzyme, e.g., neuraminidase. The luciferin conjugate is normally synthesized by using a large quantity of luciferin. Normally, there is still significant amounts of free luciferin, e.g., up to 90%, which remains free after conjugation reaction and has not been incorporated into the conjugate. This free firefly luciferin remains a significant contaminant that contributes to high background even after careful HPLC purification. This is because even if the free firefly luciferin accounts for only 0.1% in the purified conjugate, there is still 0.1 ng of free firefly luciferin if 1 microgram of conjugate is used in a reaction. The presence of even 0.1 ng of free firefly luciferin can generate significant background signal.

The inventors discovered that the background signal from the contaminating free firefly luciferin gradually decreases over a period of several hours even at refrigerated conditions in the master mix for real time detection of neuraminidase, which contains reagents for both the neuraminidase and firefly luciferase reactions. This is because the contaminating free firefly luciferin is consumed by the firefly luciferase. Thus, the use of a reagent mix for real time neuraminidase detection provides another advantage in that it allows the removal of contaminating free firefly luciferin with a simple method. A preferred embodiment involves the incubation of the reagent mix for real time detection for an appropriate period of time at room temperature or at refrigerated temperature until the background signal reaches acceptable level before being lyophilized or frozen during manufacturing. The incubation time is at least 2 hours, at least 4 hours, at least 6 hours, or at least 8 hours. The most convenient and thus preferred incubation condition is an overnight incubation at 2-8° C. or refrigerated temperature. It is understood that the amounts of firefly luciferase and other components in the reagent mix need to be optimized to account for the loss of activity during the incubation. An example of the reagent mix for real time detection and its manufacturing are described in EXAMPLE 2.

Figure 15:
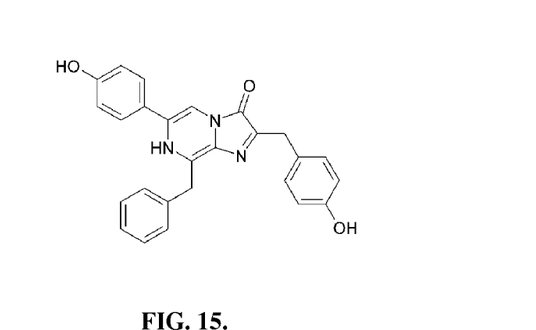
FIG. 15 is a diagram depicting the chemical structure of coelenterazine.
Figure 16:
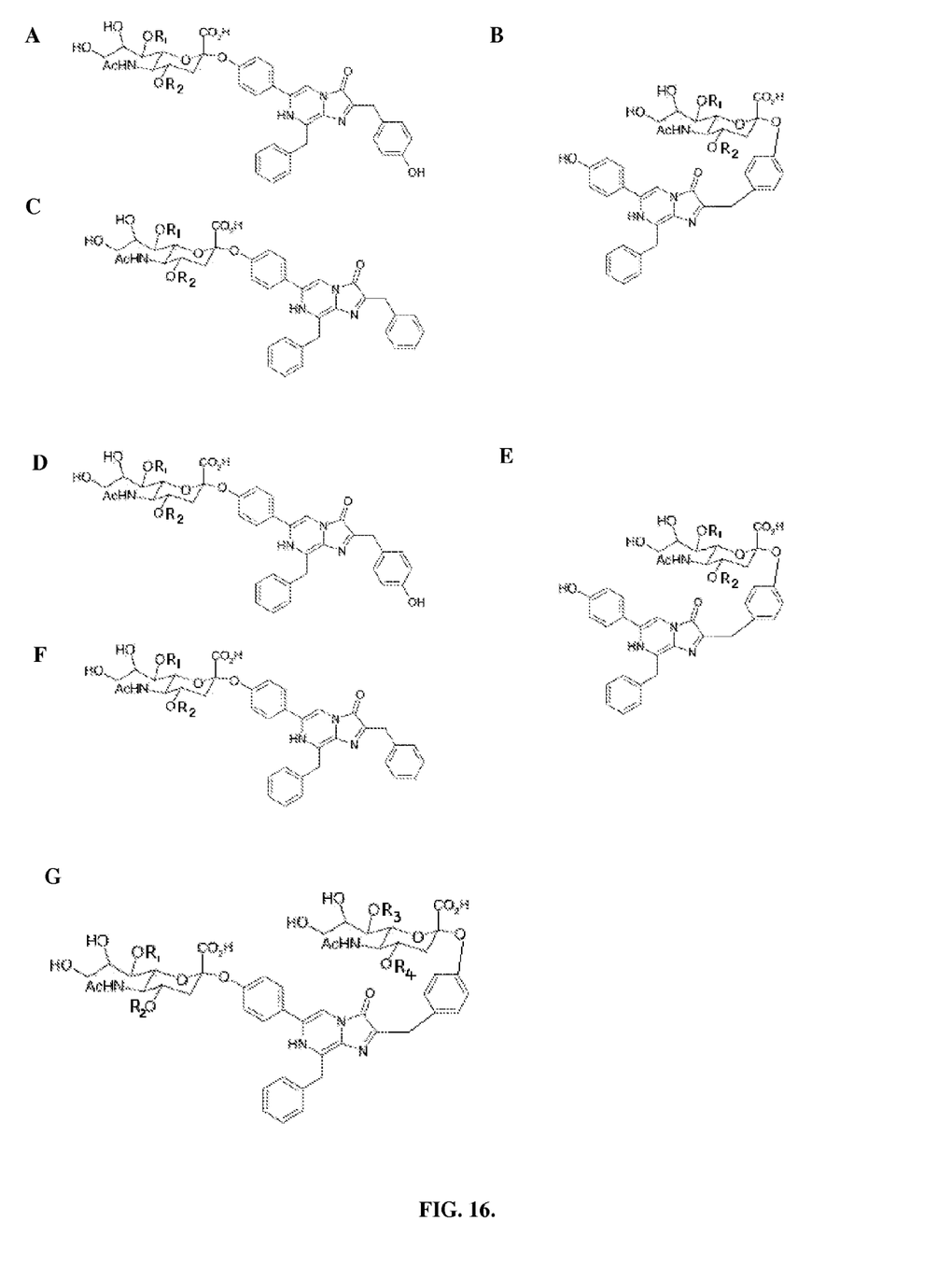
FIG. 16 (A-G) is a diagram depicting the chemical structures of the conjugates between N-acetylneuraminic acid and coelenterzine or its derivatives that are appropriate for use as substrates for neuraminidase detection, wherein R1, R2, R3, R4=H or alkyl group such as methyl group.

Coelenterazine and its conjugates are depicted in FIG. 15 and FIG. 16.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

Test Kit Formulation and Influenza Virus Detection

Synthesis of N-acetylneuraminic acid-Firefly Luciferin Conjugate

Methods for synthesizing the conjugate depicted in FIG. 3, or similar conjugates, can be derived from existing methods. For example, a method for synthesizing N-acetylneuraminic acid-dioxetane conjugate, described in a publication (e.g., Analytical Biochemistry 280, 291-300), can be used for synthesis of the conjugate depicted in FIG. 3, or similar conjugates. An example for the synthesis of the N-acetylneuraminic acid-firefly luciferin conjugate is described as follows: Methyl (5-acetamido-4,7,8,9-tetra-O-acetyl-3,5-dideoxy-D-glycero-b-D-alactononulopyranosyl chloride) Onate was prepared in two steps from a commercially available N-acetylneuraminic acid as described a publication (Analytical Biochemistry 280, 291-300), which is cited here solely for reference. The crude chloride was purified by a silica gel plug, and eluted with 200 mL of 80-90% EtOAc in hexanes. After concentration of the filtrate, the chloride was obtained as a white powder and immediately used for the next coupling reaction.

Luciferin (0.83 g) and the phase transfer catalyst tetrabutylammonium hydrogen sulfate (2.43 mmoles) was placed in a 100-mL round-bottomed flask and treated with 12.5 mL of $CH_2Cl_2$ and 17.5 mL of 0.5N NaOH at room temperature, which forms a two phase mixture. 1.24 grams of the chloride prepared as described above was dissolved in 5 mL of $CH_2Cl_2$ and added to the mixture. After an hour of vigorous stirring, the reaction mixture will be diluted with $CH_2Cl_2$ and loaded into a separator funnel that contains saturated sodium bicarbonate solution. After the organic layer is separated, the aqueous layer is further extracted twice with $CH_2Cl_2$. The combined organic layers was washed with $H_2O$ and dried over anhydrous $Na_2SO_4$. The organic solution was treated with 10 drops of $Et_3N$ and concentrated. The crude product was purified by the silica gel chromatography.

The resulting pyranoside was deprotected at 0° C. for 5 minutes in a mixture of 6.5 mL of THF, 6.5 mL of MeOH and 12 mL of 1 N NaOH. The mixture was further stirred at room temperature for an hour, followed by addition of 1.05 g solid sodium bicarbonate to lower the pH. The solution was filtered using a Buchner funnel, rinsed with a small volume of water, and pooled together for reverse-phase preparative HPLC purification.

Purification of the Conjugate

The peak identity and profile were first established using an analytical/semi-preparative Mass spectrometry-HPLC (MASS-HPLC) and a column similar to a C-18 column. The peak corresponding to the expected molecular weight was collected and used in an assay to detect bacterial neuraminidase using a two step assay, which is similar to what is described below. This peak was subsequently used as a "standard" to guide preparative HPLC purification.

A preparative HPLC with C-18 column was used for relatively large scale substrate purification using an isogradient mobile phase solution (1% ammonium acetate, pH 7.0: methanol=20%:80%). The expected peak was collected and confirmed with an analytical HPLC by comparing the retention time of the standard. The peak was collected and pooled from multiple runs. Based on analytical HPLC, the purity of the substrate was more than 98%. The substrate concentration was estimated spectrophotometrically using luciferin as the standards (absorbance wavelength 336 nm).

Use of the Conjugate for Influenza Virus Detection

The protocol described here is a two-step assay, i.e., the neuraminidase reaction and firefly luciferase reaction are carried out sequentially in two steps. Approximately 1 μg of conjugate was incubated at 37° C. for 15 minutes with 0, 0.5, 5, 50, 500 or 5,000 $TCID_{50}$ units of influenza virus (A/WS/33) in a 25 μL reaction solution (32.5 mM MES, pH 6.5, 4 mM $CaCl_2$, 0.65% Triton X-100). 12.5 μL of the reaction solution was mixed with 100 μL of luciferase reaction solution (20 nM recombinant firefly luciferase, 4 mM ATP, 13.4 mM $MgSO_4$, 100 mM Trizma, pH 7.9, 4% mannitol, and 1% sucrose) and measured for light signal using a luminometer (Sirius purchased from Berthold). Total light output was collected by integrating RLU over a period of 30 seconds.

Figure 6:
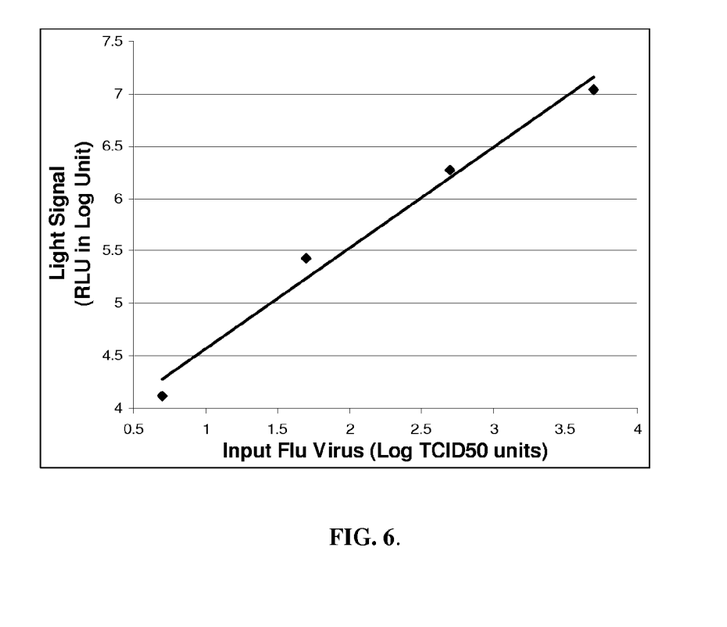
FIG. 6 is a graph showing chemiluminescence as a function of flu virus input in the detection of the influenza virus using the N-acetylneuraminic acid-firefly luciferin conjugate. Assay conditions are described in Example 1.

As shown in FIG. 6, 50 $TCID_{50}$ units of influenza virus could result in significantly more signal in comparison with the negative control. In addition, linear response of the signal was also observed over the entire range that was tested.

An Influenza Virus Detection Kit

In this example, the influenza test kit contains three key components: the capture reagent, conjugate mix and detection mix. In addition to the key components, there are two accessory components: deionized water and wash buffer. Examples of the compositions of these components are listed below:

Capture Reagent 10 mg/mL influenza virus specific antibody (polyclonal or monoclonal) coated magnetic particles in 0.1% sodium azide Conjugate Mix (Lyophilization is Preferred)

| | |
|---|---|
| MES, pH 6.5 | 32.5 mM |
| $CaCl_2$ | 4 mM |
| BSA | 1 miligram/mL |
| Triton X-100 | 0.5% |
| Mannitol | 4% |
| Sucrose | 1% |
| Conjugate | 10 microgram/mL |

Detection Mix (Lyophilization is Preferred)

| | |
|---|---|
| Trizma, pH 7.8 | 100 mM |
| $MgSO_4$ | 15 mM |
| BSA | 1 mg/mL |
| ATP, Na Salt | 12 mM |
| $NP_{40}$ or Equivalent | 0.1% |
| DTT | 10 mM |
| Co-enzyme A | 1 mM |
| EDTA, Na Salt | 2 mM |
| Mannitol | 4% |
| Sucrose | 1% |
| Firefly Luciferase | 2-4 micrograms/mL |

Wash Buffer 0.5×PBS

Deionized Water

Deionized water is used to suspend the conjugate mix and detection mix if these components are in a lyophilized form.

Detection Protocol

The influenza virus detection assay comprises essentially three steps: 1) influenza virus capture, 2) cleavage of sialic acid-firefly luciferin conjugate with influenza neuraminidase, and 3) detection of released firefly luciferin. Specifically one can use the following basic protocol:

1. Add 100 μL of capture particles (1 mg of capture reagent) to 1.0 mL sample. In this example, the capture reagent is magnetic particles coated with an influenza virus specific antibody.
2. Incubate at room temperature for 5-10 minutes.
3. Wash the reagent twice with 1 mL wash buffer using a magnet.
4. Suspend the washed capture reagent, now bound with flu virus if there is influenza virus in the sample, in 100 μL conjugate solution, which will lyse the virus because of the presence of Triton X-100.
5. Incubate at room temperature for 10-15 minutes.
6. Using a magnet, recover and transfer the supernate (100 μL) to 100 μL firefly luciferase reaction solution preloaded into a detection tube, or a lyophilized detection mix in a detection tube.
7. Place the detection tube into a luminometer and record the light signal (relative light unit) for an appropriate period of time (e.g., 30 seconds).

Note that firefly luciferase mediated biochemiluminescence reaction is of a glow light type, which stably emits light for at least 5 minutes. Therefore, there is no need to use a luminometer with an automated injector.

EXAMPLE 2

Real Time Detection of Influenza Viral Neuraminidase Using the Neuraminic Acid-Firefly Luciferin Conjugate for the Detection of Influenza Virus In this example, influenza viral neuraminidase activity is detected at real time, i.e., neuraminidase reaction and biochemiluminescence reaction are combined in a single reaction tube and carried out simultaneously. A master mix that contains all necessary components except for neuraminidase and free firefly luciferase was formulated according to the composition for the Detection Mix (see below). After adjusting the pH to 7.0 to 7.2 and the final volume, the mix is stored at 2-8° C. overnight, which allows the luciferase consume the contaminating free luciferin and thus reduces the background. The detection mix is then aliquoted into vials (1.0 mL each), lyophilized, and stored at −20° C.

For influenza virus detection, one vial of the lyophilized detection mix is suspended in 0.9 mL of buffer containing 1% Triton X 100 or NP-40 equivalent, and 5 μL/mL Antifoam A (Sigma). Prior to detection, 90 μL of the reconstituted detection mix was transferred to a detection tube. 10 μL of sample was added to the detection mix, followed by luminometer reading for a period of 60 minutes to document the reaction kinetics.

Figure 7:
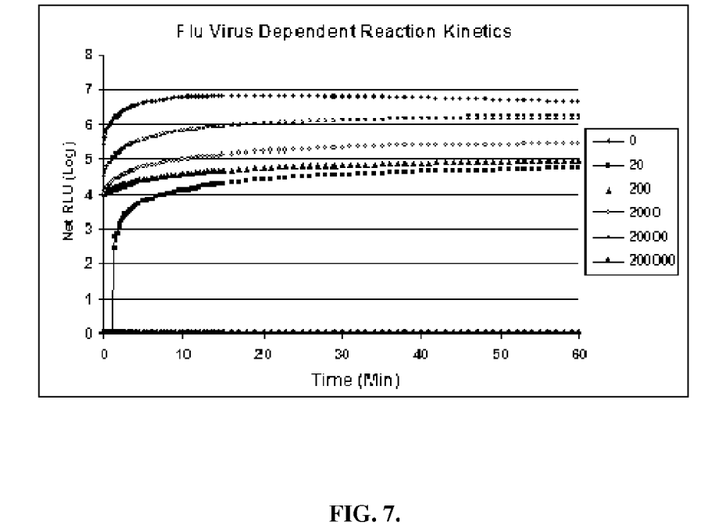
FIG. 7 is a graph showing the reaction kinetics in a real time assay, which both the neuraminidase and luciferase reaction occur simultaneously in the same detection tube. Assay conditions are described in Example 2. The reactions were initiated by adding influenza virus to the detection mix. The reaction kinetics over a period of 60 minutes was recorded using a luminometer. The light signal was measured once every 10 seconds. The numbers in the column in the figure are the input influenza virus amounts in $TCID_{50}$ units.

FIG. 7 depicts the reaction kinetics of an assay that was performed using a protocol that is substantially similar to that described above. As shown, the signal intensity increased rapidly in the first 10 minutes in the presence of influenza virus, followed by a period of plateau that lasted up to at least 60 minutes. The reactions reached plateau at 10 minutes, after which the light signal intensity remained fairly constant. For all reactions with input influenza virus, little or no decrease in signal intensity was observed even at 60 minutes (FIG. 7). Thus, test results obtained at any time point between 10 and 60 minutes are likely to be valid.

An Influenza Virus Detection Kit

According to this example, the influenza test kit for this assay format contains two key components: the capture reagent and detection mix, the latter containing both the conjugate and all necessary reagents for firefly luciferase catalyzed biochemiluminescence except for firefly luciferin. In addition to the key components, there are two accessory components: Virus Lysis Buffer and Wash Buffer. Examples of the compositions of these components are listed below:

Capture Reagent
  10 mg/mL influenza virus specific antibody coated magnetic particles in 0.1% sodium azide
Detection Mix (Lyophilized Form is Preferred)

| Imidazole, pH 7.0 | 50 mM |
| BSA | 1 mg/mL |
| ATP, Na Salt | 12 mM |
| DTT | 10 mM |
| Co-enzyme A | 1 mM |
| $MgSO_4$ | 15 mM |
| $CaCl_2$ | 4 mM |
| Mannitol | 4% |
| Sucrose | 1% |
| Conjugate | 10 µg/mL |
| Firefly Luciferase | 4-5 µg/mL (thermal stable firefly luciferase is preferred. Thermal stable firefly luciferase is available from commercial vendors such as Promega.). |

Wash Buffer
0.5×PBS
Virus Lysis Buffer

| Imidazole, pH 7.0 | 10 mM |
| Triton X-100 | 0.5% |

Preparation of the Detection Mix

The detection mix is prepared by mixing stock solutions of the reagents listed above with deionized water (approximately 70%). The pH of the mix solution is adjusted with 1 N NaOH or KOH to between 7.0 and 7.2. The solution is then adjusted to the final volume with deionized water, stored overnight at 2-8° C., aliquoted 0.5 mL (or other desired volume) into appropriate lyophilization vials, lyophilized, and stored at appropriate temperature (e.g., at or below −20° C. for long term storage).

Detection Protocol

The influenza virus detection assay comprises essentially two steps: 1) influenza virus capture and 2) cleavage of neuraminic acid-firefly luciferin conjugate with influenza neuraminidase and simultaneous detection of the released firefly luciferin. Specifically one can use the following basic protocol:

1. Bring the lyophilized detection mix reagent to room temperature.
2. Add 100 µL of capture particles (1 mg of capture reagent) to 1.0 mL sample. In this example, the capture reagent is magnetic particles coated with influenza specific antibody.
3. incubate at room temperature for 5-10 minutes.
4. Wash the reagent twice with 1 mL wash buffer using a magnet.
5. Suspend the washed capture reagent, now bound with influenza virus if there is influenza virus in the sample, in 500 µL virus lysis solution, which lyses the virus because of the presence of Triton X-100.
6. Using a magnet, recover and transfer the supernate (500 µL) to the lyophilized detection mix. Mix, transfer the solution to a detection tube, and incubate at room temperature for 5-10 minutes.
7. Place the detection tube into a luminometer and record the light signal (relative light unit) for an appropriate period of time (e.g., 120 seconds).

Note that the detection mix can be suspended in 0.25 mL of lysis buffer to make 2× solution. Smaller amounts such as 25 microliters can be used to mix 25 microliters of samples such as culture influenza virus for detection. The influenza virus capture step can be eliminated if a specific substrate, such as the one that is depicted in FIG. 4, is used. In this case, the assay procedure becomes essentially one step.

EXAMPLE 3

Use of Antibodies to Inhibit Non-Specific Neuraminidase Activity in an Influenza Viral Neuraminidase Assay The commonly used clinical samples for influenza detection are throat and nasal swabs. Some bacterial species that are found in nasal or oral can also secret neuraminidase. These bacterial species include *Streptococcus pneumoniae* and *Actinomyces viscosus*. In this example, monoclonal or polyclonal antibodies specific for the neuraminidases for these bacterial species are added to the conjugate mix in Example 1 or the lysis buffer or detection mix in Example 2. Bacterial neuraminidase in the sample, if any, is blocked by the antibodies thereby reducing the background. The optimal amounts of antibodies need to be determined experimentally.

EXAMPLE 4

Diagnosis of Influenza Infection Using an N-Acetylneuraminic Acid-Luciferin as the Chemiluminescent Substrate and an Influenza Viral Neuraminidase Inhibitor As discussed, the neuraminic acid-firefly luciferin depicted in FIG. 3 is not specific for a particularly source of neuraminidase. However, highly specific inhibitors for influenza virus neuraminidase such as oseltamivir are available. To perform specific detection of influenza virus in a sample, two forms of the detection mix disclosed in EXAMPLE 2 need to be formulated. One form contains no influenza neuraminidase inhibitor (Detection Mix 1) and the other contains the inhibitor (Detection Mix 2). A clinical sample such as nasal swab is split into two portions. In a parallel detection, one portion of the sample is mixed with Detection Mix 1 whereas the other portion is mixed with Detection Mix 2, followed by detection of lights signal as described in EXAMPLE 2.

If both are positive, it indicates that either the sample is contaminated with other bacterial neuraminidase or there is other viral infection such as infection with parainfluenza virus, which also has neuraminidase activity. If Detection Mix 1 is positive while Detection Mix 2 is negative, then it indicates that there is influenza virus infection. If both are negative, then it indicates that there is no infection with influenza virus or parainfluenza virus.

EXAMPLE 5

Diagnosis of Bacterial Vaginosis Using an N-Acetylneuraminic Acid-Luciferin as the Chemiluminescent Substrate In this example, an N-acetylneuraminic acid-firefly luciferin conjugate is used as the chemiluminescent substrate for detection of bacterial vaginosis. A detection mix similar to that described in Example 2 can be used for this purpose. However, it is understood that the detection mix may need to be optimized for bacterial vaginosis detection since sialidase activity in a vaginal sample may be considerably higher than that for a sample for influenza detection.

The detection mix solution described in Example 2 is used to demonstrate the detection of bacterial vaginosis. The Osom BV blue positive control and negative control (from Genezyme Diagnostics), which contain different levels of bacterial sialidase, are used to demonstrate the use of the detection mix for bacterial vaginosis detection. 40 microliters of the control sample at various dilutions (1:10, 1:100, 1:1000, and 1:10000) was spiked into a Hygiena Snapshot swab, which was placed in 500 microliters of detection mix described in Example 2 and immediately placed in a handheld luminometer (Hygiena) for detection. Four replicates were tested with each dilution sample and with the negative control as well. Total assay time: <2 min.

For comparison, the same samples were also tested with a competing, FDA approved product (the BV Blue test) that is based on colorimetric method, which is a qualitative method, involves two steps and takes about 15 minutes. The data is presented in Table 1.

TABLE 1

Detection of BV Blue Positive Control with the Detection Mix.

| Sample | Test Result (RLU) (Repeat #) | | | | Color Based Method |
|---|---|---|---|---|---|
| | 1 | 2 | 3 | 4 | (BV Blue) |
| No sample | 59 | 52 | 52 | 55 | Negative |
| 40 uL of negative control | 52 | 60 | 53 | 58 | Negative |
| 40 uL of positive control-1:10000 Diluted | 100 | 84 | 97 | 108 | Negative |
| 40 uL of positive control-1:1000 Diluted | 566 | 242 | 401 | Not tested | Negative |
| 40 uL of positive control-1:100 Diluted | 4400 | 4723 | 5298 | 4937 | Negative |
| 40 uL of positive control-1:10 Diluted | 9460 | 9311 | 9251 | 9156 | Positive/Negative |
| 40 uL of positive control-1:5 Diluted | | | Not tested | | Weak Positive |
| 40 uL of positive control-Undiluted | 9671 | 9655 | 9609 | 9560 | Positive |

For detection that uses a patient sample, i.e., vaginal swab, the vaginal swab can be first rinsed in a sample buffer, e.g., 1 mL of 1×PBS buffer, which or a portion of which is mixed with the detection mix in solution form or, preferably, in lyophilized form in a test tube. The test tube is placed in a luminometer for detection. It is understood that a cutoff value in terms of light signal intensity (RLU) needs to be established by testing a large number of negative and positive samples, preferably more than 100 positive samples and 100 negative samples.

EXAMPLE 6

Diagnosis of Chagas' Disease Using an N-Acetylneuraminic Acid-Luciferin as the Chemiluminescent Substrate Chagas' disease (also called American trypanosomiasis) is a human tropical parasitic disease, which occurs in the Americas, particularly in South America. Its pathogenic agent is a flagellate protozoan named *Trypanosoma cruzi*, which is transmitted to humans and other mammals mostly by blood-sucking bugs of the subfamily Triatominae (Family Reduviidae). The cell invasion form of *T. cruzi*, Trypomastigote, expresses high levels of trans-sialidase activity; therefore, measurement of sialidase level can be used for diagnosis of active *T. cruzi* infection and for monitoring disease or therapeutic progress.

As in the bacterial vaginosis diagnostic test, the N-acetylneuraminic acid-luciferin including their derivatives, e.g., the one depicted in FIG. 2, can be used for detection of *T. cruzi* infection Chaga's disease.

There are several different types of *T. cruzi* infection status: 1) acute infection, which is an acute phase of an infection, 2) chronic active infection, which an infection with persistent and active infection, and 3) cleared or dormant infection, which is an infection without active infection but with detectable antibodies specific for the protozoa.

For diagnosis of acute and active or chronic infection, sialidase activity in plasma or serum is measured using the chemiluminescent assay described in this invention. Elevated sialidase activity in plasma or serum indicates active *T. cruzi* infection. In an active infection assay, serum or plasma sample with appropriate dilution in a buffer (e.g., PBS buffer) as determined with experiments is added to a detection mix as described in Example 2. The detection mix is preferably lyophilized for long-term storage. The output signal is then measured with a luminometer. Again, a cutoff value needs to be established by testing a large number of negative samples, e.g., 100 or more of negative samples. Sensitivity of the assay can be determined by testing a large number of positive samples, e.g., 100 or more of positive samples confirmed with another method such as polymerase chain reaction (PCR) method.

*T. cruzi* infection may be cleared by the host but still results in detectable antibodies, which can be detected with a neutralization assay that uses the same detection mix as for an active infection test except that the detection mix also contains small amounts of *T. cruzi* sialidase. In the absence of specific antibodies in a serum or plasma sample, the *T. cruzi* sialidase in the detection mix generates a detectable light signal at certain level. In the presence of specific antibodies in a serum or plasma sample, a reduction of the signal can be detected. Thus, a reduction of the signal indicates chronic, cleared or dormant infection. Again, a cutoff value needs to be established by testing a large number of negative samples, e.g., 100 or more of negative samples. Sensitivity of the assay can be determined by testing a large number of positive samples, e.g., 100 or more of positive samples confirmed with another method such as an ELISA test.

EXAMPLE 7

Chemiluminescent Proline Aminopeptidase Assay for Bacterial Vaginosis Diagnosis Detection Elevated proline aminopeptidase activity in vaginal fluid has been associated with bacterial vaginosis. Thus, a praline aminopeptidase assay can also be used to diagnose bacterial vaginosis. Proline aminopeptidase (or called proline iminopeptidase) is a hydrolase that cleaves the L-proline residues from the N-terminal position in peptides.

A substrate that can be used in a proline aminopeptidase assay for bacterial vaginosis diagnosis is L-proline-6-amino firefly luciferin conjugate (L-prolyl-6-amino firefly luciferin, FIG. 8) or its derivatives. In a proline aminopeptidase assay, the enzyme cleaves the synthetic substrate and releases the free 6-amino firefly luciferin, which can be quantitatively detected in a chemiluminescence reaction in the presence of firefly luciferase and ATP. It can be a one-step assay or two step assays in a fashion similar to those described in the influenza or bacterial vaginosis sialidase assay (Examples 1 and 2).

Figure 8:
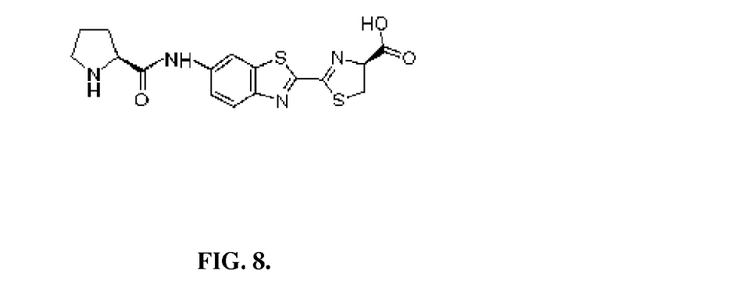
FIG. 8 is a diagram depicting the chemical structure of a L-proply-6-amino firefly luciferin conjugate.

The linkage between the L-proline and firefly luciferin is a peptide bond (FIG. 8). Thus, synthesis of this group of conjugates can be accomplished using peptide synthesis chemistry, which is well known to the skilled in the art. The substrate can be purified using HPLC and C-18 column by following a protocol similar to that described in EXAMPLE 1 for the purification of N-acetylneuraminidase-firefly luciferin conjugate. Likewise, formulation of detection mix and detection protocol can also be derived from those described in Examples 1 and 2. For clinical diagnosis use, again a cutoff value needs to be established by testing a large number of negative samples, e.g., 100 or more of negative samples. Sensitivity of the assay can be determined by testing a large number of positive samples, e.g., 100 or more of positive samples.

EXAMPLE 8

Chemiluminescent Assays for Leukocyte Esterase Detection

Elevated leukocyte esterase (LE) activity in urinary track indicates the presence of white blood cells and other abnormalities associated with infection or inflammation, e.g., urinary track infection. Therefore, leukocyte esterase test (LE test) is widely used to diagnose active urinary tract infection. LE tests are also used to screen for gonorrhea infection, colpitis, amniotic fluid infections, bacterial meningitis, and ascite or hydrothorax infection by testing leukocyte esterase activity in appropriate samples. Current tests generally suffer from insufficient sensitivity and/or quantitation capability and consequently have limited clinical utility.

The present invention discloses chemiluminescent substrates and methods for leukocyte esterase test. The appropriate substrates are carboxylic acid-firefly luciferin conjugates such as acetyl firefly luciferin. The —COOH group of the carboxylic acid are coupled with the 6-OH group of the firefly luciferin to generate an ester bond. Suitable carboxylic acids include, but are not limited to, alkyl substituted carboxylic acid such as formic acid, acetic acid, propionic acid, butyric acid and etc. as well as aromatic acid such as benzoic acid. The esterase hydrolyzes the ester bond of the conjugate to release free firefly luciferin, which becomes a substrate for luciferase in a biochemiluminescent reaction that generates a light signal.

In certain embodiments, the substrate are the firefly luciferin-alcohol conjugates, which is the ester formed by coupling the —COOH group of firefly luciferin with the —OH of an alcohol, resulting in, for example, firefly luciferin methyl ester or firefly luciferin ethyl ester. The alcohol can be either alkyl alcohol such as methanol, glycerol or aromatic alcohol such as benzyl alcohol. The esterase hydrolyzes the ester bond of the conjugate to release free firefly luciferin, which becomes a substrate for luciferase in a chemiluminescent reaction that generates a light signal. Elevated light signal indicates high LE activity, which in turn is indicative of an active infection.

Figure 9:
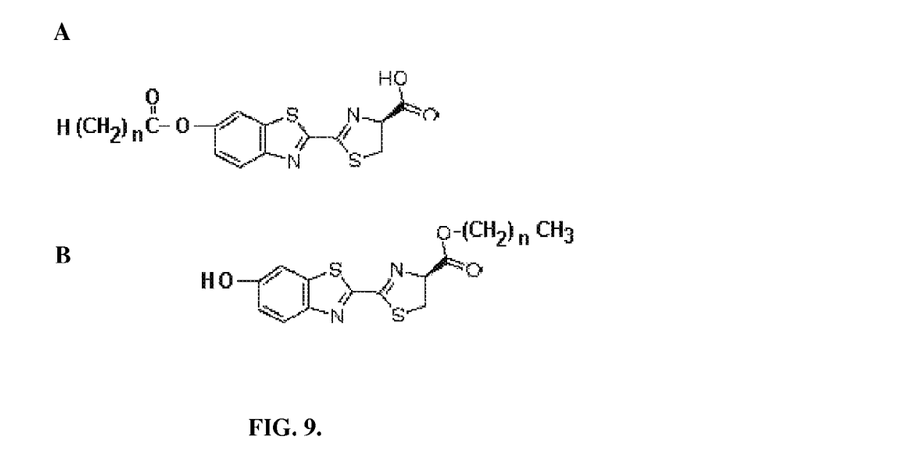
FIG. 9 is a diagram depicting the chemical structures of (A) a carboxylate firefly luciferin ester conjugate and (B) an alcohol-firefly luciferin ester for detection of leukocyte esterase.

Examples of firefly luciferin-carboxylate conjugate and firefly luciferin-alcohol conjugate are depicted in FIG. 9. Methods for synthesizing these esters are well known to the skilled in the art. Purification of the ester can also be accomplished using HPLC in a fashion similar to the purification strategy described in EXAMPLE 1 for the purification of N-acetylneuraminic acid-firefly luciferin. Formulation of the detection mix can be derived from the protocol described in EXAMPLE 1 or 2 as well.

For clinical use, again a cutoff value needs to be established by testing a large number of negative samples, e.g., 100 or more of negative samples. Sensitivity of the assay can be determined by testing a large number of positive samples, e.g., 100 or more of positive samples.

EXAMPLE 9

Chemiluminescent Alpha-L-Fucosidase (AFU) Assays

The alpha-L-fucosidase (AFU) assay is for the determination of AFU activity in patient serum samples. AFU is a lysosomal enzyme involved in the degradation of a diverse group of naturally occurring fucoglycoconjugates. Serum AFU activity is considered a useful marker of hepatocellular carcinoma (HCC). Elevated AFU levels in serum are an early indication of HCC. Though measurement of serum fetoprotein (AFP) is a common practice for early detection of HCC, use of AFP assay alone suffers from its low specificity and sensitivity, due to the fact that not all HCC secrete AFP. AFP levels may be normal in as many as 40% of patients with early HCC and 15-20% of patients with advanced HCC. Recent studies have clearly demonstrated that measurements of both AFP and AFU can significantly increase the detection specificity and sensitivity for HCC. AFU is reported to be a more sensitive marker, especially for detecting a small tumor size of HCC. It has also been shown that abnormal AFU level exists in serum samples from patients suffering from adult leukemia or ovarian carcinoma. In addition, AFU level is also high in patients suffering from liver cirrhosis and chronic hepatitis.

Figure 10:
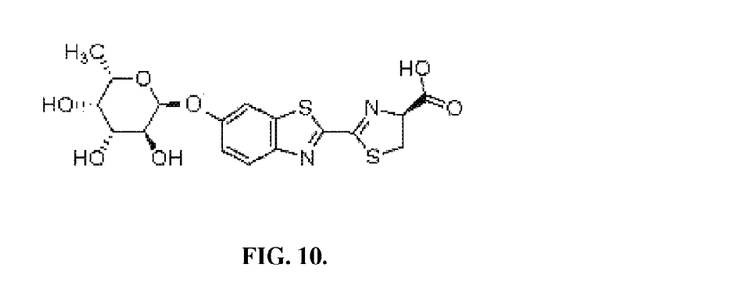
FIG. 10 is a diagram depicting the chemical structure of alpha-L-fucopyranoside-firefly luciferin conjugate for detection of alpha-L-fucosidase.

According to the present invention, AFU level in a sample is quantified using a synthetic substrate alpha-L-fucopyranoside firefly luciferin conjugate, whose chemical structure is best understood by referring to FIG. 3, which depicts a conjugate between neuraminic acid and firefly luciferin. In the alpha-L-fucopyranoside-firefly luciferin conjugate, the neuraminic acid portion in FIG. 3 is replaced with alpha-L-fucopyranoside. An example of the conjugate is depicted in FIG. 10.

In a chemiluminescent AFU assay, alpha-L-fucopyranoside-firefly luciferin conjugate is cleaved by alpha-L-fucosidase in a sample to release free firefly luciferin, which can be quantified in a chemiluminescence reaction in the presence of firefly luciferase, ATP and other appropriate conditions. It can be a one-step assay or two steps assay as those described in EXAMPLES 1 and 2.

Synthesis and purification of alpha-L-fucopyranoside-firefly luciferin conjugate can use a protocol similar to that for synthesis and purification of N-acetylneuraminic acid-firefly luciferin conjugate as described in EXAMPLE 1.

The assay kit can be similar to those used for neuraminidase detection except the substrate is firefly luciferin-alpha-L-fucopyranoside instead. The detection mix, either one step or two step form, can be formulated according to the formula and protocols described in EXAMPLES 1 and 2. The assay protocol can be readily adopted from the influenza neuraminidase test or bacterial vaginosis test described above by a skilled in the art.

EXAMPLE 10

Chemiluminescent GPDA Assays

Elevated glycylproline dipeptidyl aminopeptidase (GPDA) activity in blood and urine is associated with abnormality in liver, stomach, intestine and kidney. Elevated GPDA activity (especially the isoenzyme, GPDA-F) in serum has been identified as a reliable marker enzyme for hepatocellular carcinoma and other liver disease.

Figure 11:
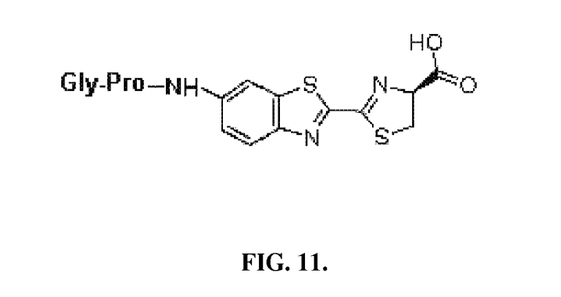
FIG. 11 is a diagram depicting the chemical structure of L-glycyl-L-prolyl-6 amino firefly luciferin conjugate for detection of glycylproline dipeptidyl aminopepdidase (GPDA).

The GPDA assay in the current invention is based on the enzymatic cleavage of the synthetic substrate L-glycyl-L-prolyl-6-amino firefly luciferin (FIG. 11), whose chemical structure is similar to that of L-prolyl-6-amino firefly luciferin. In the L-glycyl-L-prolyl-6-amino firefly luciferin conjugate, the peptide moiety is L-glycyl-L-proline. Synthesis and purification can also be accomplished using methods similar to those for L-prolyl-6-amino firefly luciferin conjugate.

In the GPDA assay, the L-glycyl-L-prolyl-6-amino firefly luciferin conjugate is cleaved by GPDA to give rise to free luciferin, which is detected in a firefly luciferase catalyzed chemiluminescence reaction. It can be a one-step assay or two steps assay as described in Examples 1 and 2. Reagent and kit formulation can be similar to those described in Examples 1 and 2 as well.

For clinical use, again a cutoff value can be established by testing a large number of negative clinical samples, e.g., 100 or more of negative samples. Sensitivity of the assay can be determined by testing a large number of positive clinical samples, e.g., 100 or more of positive samples. The positive samples are those from patients who are confirmed positive for hepatocellular carcinoma (HCC) with other well-recognized methods.

EXAMPLE 11

Chemiluminescent Assays for *Candida* Yeast Detection

Many of the yeast *Candida* species, particularly *Candida albican*, contain a unique enzyme, beta-galactosaminidase. The *Candida* species, particularly *Candida albican*, are the most common pathogens that cause yeast vaginal infection. Thus, a substrate for beta-galactosaminidase would be useful for detecting *Candida* species infection.

Figure 12:
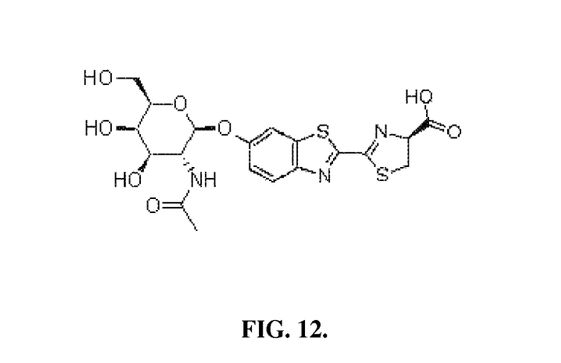
FIG. 12 is a diagram depicting the chemical structure of firefly luciferin-N-acetyl-beta-D-galactosaminide conjugate for detection of Beta-D-galactosaminidase.

The suitable substrates for firefly luciferase catalyzed biochemiluminescence reaction is a conjugate between beta-galactosaminidase and firefly luciferin (firefly luciferin-N-acetyl-beta-D-galactosaminide), which are linked together through an appropriate chemical bond that can be cleaved by beta-galactosaminidase. Example of a substrate is shown in FIG. 12.

In the presence of beta-galactosaminidase in a sample, the conjugate is cleaved to release free firefly luciferin, which is detected in a firefly luciferase catalyzed biochemiluminescence reaction. Formulations of the reagents and test kits and detection procedures can be adopted from those described in Examples 1 and 2 for neuraminidase detection using N-acetylneuraminic acid-firefly luciferin conjugate. Again, a large number of clinical samples need to be tested to established the cutoff value for a yeast infection, e.g., vaginal yeast infection.

In addition to beta-galactosaminidase, *Candida albicans* produces L-proline aminopeptidase. Thus, to further differentiate the infection between *Candida albicans* and other *Candida* species, both enzymes can be assayed. A biochemiluminescence substrate for L-proline aminopeptidase and its use for L-proline aminopeptidase detection are described in EXAMPLE 7. A sample with elevated activities for both enzymes is considered positive for *Candida albicans* infection. The cutoff values for both enzymes can be established by testing a large number, e.g., 100, of negative samples and a large number, e.g., 100, of positive samples.

Formulations of the reagents and test kits and detection procedures can be adopted from Examples 1 and 2 for neuraminidase detection using N-acetylneuraminic acid-firefly luciferin conjugate.

EXAMPLE 12

A Chemiluminescent Assay for Lipid Esterase and *Salmonella* Species Detection

The *Salmonella* esterase catalyzes the hydrolysis of a variety of C6 to C16 fatty acid esters but does not hydrolyze peptide bonds. Presence of this esterase activity is indicative of *Salmonella* species presence in a sample.

Figure 13:
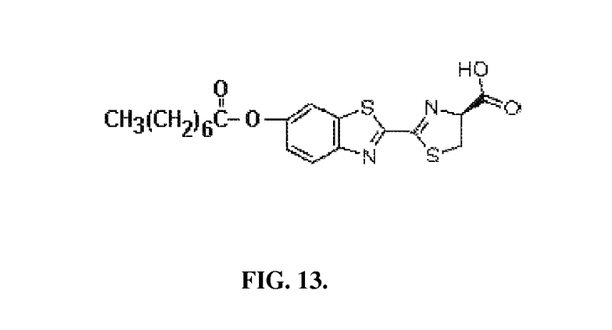
FIG. 13 is a diagram depicting the chemical structure of a fatty acid-firefly luciferin ester conjugate for detection of Salmonella lipid esterase.

The current invention relates to novel chemiluminescent C6 to C16 fatty acid ester esterase substrates that can be used to detect *Salmonella*. The *Salmonella* esterase can cleave the substrates and release the chemiluminescent moiety firefly luciferin, which is detected in a luciferase-catalyzed reaction. The substrates useful for the current invention are firefly luciferin fatty acid ester (C6 to C16 fatty acid). The —COOH group of the fatty acid are coupled with the 6-OH group of the firefly luciferin to generate an ester. An example of thus an ester is depicted in FIG. 13. One preferred fatty acid is caprylic acid.

The synthesis of firefly luciferin based *Salmonella* esterase substrates can be derived from a published article or articles or text book that provides a protocol for the synthesis of a lipid ester. For example, the synthesis can be performed by incubating the firefly luciferin with excessive amounts of C6 to C16 fatty acid chloride (e.g., caprylyl chloride) in pyridine at room temperature for 1 hour, followed by silica gel column purification to remove the unreacted reactants (e.g., the fatty acid). The recovered firefly luciferin fatty acid ester will be further purified using a semi-preparative HPLC to remove the unreacted firefly luciferin and fatty acid.

EXAMPLE 13

A Chemiluminescent Assay for Hydroxyproline Aminopeptidase Detection

Vaginal samples from *Neisseria gonorrhoeae* patients show high level of hydroxyproline aminopeptidase activity.

Figure 14:
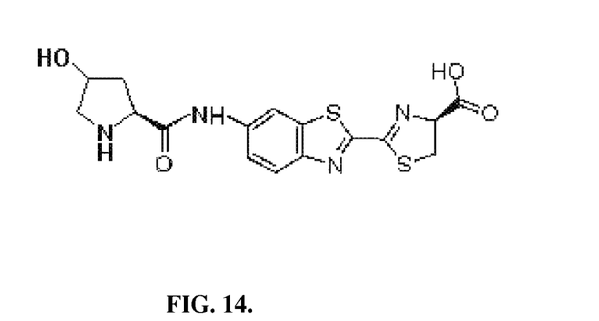
FIG. 14 is a diagram depicting the chemical structure of hydroxyproline-firefly luciferin conjugate for detection of hydroxyproline aminopeptidase.

Therefore, hydroxyproline aminopeptidase assay can be used to detect *Neisseria gonorrhoeae* infection. Hydroxyproline-firefly luciferin, depicted in FIG. 14, can be a substrate for detection of the enzyme and therefore, diagnosis of *Neisseria gonorrhoeae* infection.

Methods for substrate synthesis, purification and test kit formulation are similar to those used for praline aminopeptidase (Example 7) and to those for neuraminidase (Examples 1 and 2).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:
1. A compound of Formula II or a salt thereof

II

2. A method for detecting β-galactosaminidase in a sample, comprising:(a) contacting said sample with a compound of Formula II according to claim 1 under conditions effective for the compound to be cleaved by β-galactosaminidase to release firefly luciferin; and (b) detecting the released firefly luciferin.

3. The method according to claim 2, wherein said released firefly luciferin is detected via a biochemiluminescence reaction in the presence of firefly luciferase.

4. The method according to claim 2, wherein said β-galactosaminidase is yeast β-galactosaminidase.

5. A method for detecting *Candida* yeast in a sample, comprising:(a) contacting said sample with a compound of claim 1 under conditions effective for the compound to be cleaved by *Candida* yeast β-galactosaminidase to release firefly luciferin; and (b) detecting the released firefly luciferin.

6. The method according to claim 5, wherein said released firefly luciferin is detected via a biochemiluminescence reaction in the presence of firefly luciferase.

7. The method according to claim 5, wherein said β-galactosaminidase is *Candida albican* β-galactosaminidase.

8. A method for diagnosing yeast vaginosis in a subject in need thereof comprising
    (a) contacting a biological sample from said subject with a compound of Formula II according to claim 1 under conditions effective for the compound to be cleaved by yeast β-galactosaminidase to release firefly luciferin; and
    (b) detecting the released firefly luciferin.

9. The method according to claim 8, wherein said yeast is member of *Candida* sp.

10. The method according to claim 8, wherein said subject is a human patient or a veterinary animal.

* * * * *